United States Patent [19]

Upton et al.

[11] Patent Number: 5,506,270
[45] Date of Patent: Apr. 9, 1996

[54] VENLAFAXINE IN THE TREATMENT OF HYPOTHALAMIC AMENORRHEA IN NON-DEPRESSED WOMEN

[75] Inventors: Gertrude V. Upton, Radnor; Albert T. Derivan, Villanova; Richard L. Rudolph, Berwyn, all of Pa.

[73] Assignee: American Home Products Corporation, Madison, N.J.

[21] Appl. No.: 380,903

[22] Filed: Jan. 30, 1995

[51] Int. Cl.$^6$ .................. A61K 31/045; A01N 31/00
[52] U.S. Cl. .................. 514/730; 564/157; 564/219; 564/336; 549/443; 549/444; 514/646; 514/653; 514/659; 514/727; 514/729; 514/899
[58] Field of Search .................. 564/157, 219, 564/336; 549/443, 444; 514/646, 653, 659, 727, 729, 730, 899

[56] References Cited

U.S. PATENT DOCUMENTS

| | | | |
|---|---|---|---|
| 4,110,438 | 8/1978 | Gahwyler | 424/177 |
| 4,291,028 | 9/1981 | Vorys | 424/238 |
| 4,292,315 | 9/1981 | Vorys | 424/240 |
| 4,328,134 | 5/1982 | Schally et al. | 525/54.11 |
| 4,535,186 | 8/1985 | Husbands et al. | 564/336 |
| 4,611,078 | 9/1986 | Husbands et al. | 558/410 |
| 4,761,501 | 8/1988 | Husbands et al. | 564/167 |
| 4,826,844 | 5/1989 | Husbands et al. | 514/252 |

OTHER PUBLICATIONS

Hennert et al., The Lancet, 2, 8614, 789–790, Oct. 1, 1988.
Upton et al., Yale Journal of Biology and Medicine, 46, 314–323, (1973).
Upton, Twelfth Ann. Mtg. of the Int. Soc. of Reproductive Med. Oct. 2–4, 1980.
Berga et al., Journal of Clinical Immunoassay, 14, 1, 23–28, (1991).
Reame et al., Journal of Clinical Endocrinology and Metabolism, 61, 5, 851–858, 1985.
Balen et al., British Journal of Obstetrics and Gynaecology, 100, 1082–1089, Dec. 1993.
Berga et al., Psychiatric Clinics of North America, 12, 1, 105–116, 1989.
Molinksi, Psychother. Psychosom., 31, 283–287, 1979.
Fries et al., Am. J. Obstet. Gynecol., 118, 4, 473–479 (1974).
Schwartz, Journal of Adolescent Health Care, 7, 425 (1986).
Fava et al., Psychosomatics, 25, 12, 905–908, (1984).
Galle et al., Fertility and Sterility, 39, 5, 633–639 (1983).
Cohen et al., Am. J. Psychiatry, 151, 4, 620 (1994).
Leyendecker et al., Human Reproduction, 8, 2, 184–188, (1993).

Primary Examiner—Samuel A. Acquah
Attorney, Agent, or Firm—Steven R. Eck

[57] ABSTRACT

This invention provides a method for treating hypothalamic amenorrhea in a non-depressed female mammal by administering to the mammal an effective amount of a hydroxycycloalkanephenethyl amine compound of the following structural formula:

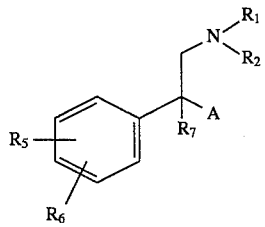

in which A is a moiety of the formula

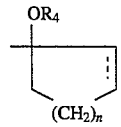

wherein the dotted line represents optional unsaturation;

$R_1$ is hydrogen or alkyl;

$R_2$ is alkyl;

$R_4$ is hydrogen, alkyl, formyl, or alkanol;

$R_5$ and $R_6$ are, independently, hydrogen, hydroxyl, alkyl, alkoxy, alkanoyloxy, cyano, nitro, alkylmercapto, amino, alkylamino, dialkylamino, alkanamido, halo, trifluoromethyl, or taken together, methylene dioxy;

$R_7$ is hydrogen or alkyl; and n is 0, 1, 2, 3, or 4;

or a pharmaceutically acceptable salt thereof.

13 Claims, No Drawings

VENLAFAXINE IN THE TREATMENT OF HYPOTHALAMIC AMENORRHEA IN NON-DEPRESSED WOMEN

This invention comprises a new use for venlafaxine. More particularly, this invention comprises a method for treating hypothalamic amenorrhea (HA) in a non-depressed female mammal, preferably in a non-depressed human female.

BACKGROUND OF THE INVENTION

The active ingredients of this invention, (1-[2-(dimethylamino)-1-(4-methoxyphenyl)ethyl]cyclohexanol), its analogues or therapeutically acceptable salts thereof, are known generally as venlafaxine. These ingredients are disclosed in U.S. Pat. No. 4,535,186 (Husbands et al.) and have been previously reported to be useful as an antidepressant. U.S. Pat. No. 4,535,186 teaches the production of venlafaxine and its analogues and is incorporated herein by reference.

Venlafaxine has been shown to be a potent inhibitor of monoamine neurotransmitter uptake, a mechanism associated not only with demonstrated clinical antidepressant activity, but also with reproductive function by affecting indirectly the hypothalamic-pituitary-ovarian axis. Due to its novel structure, venlafaxine has a mechanism of action different from other available antidepressants, such as the tricyclic antidepressants desipramine, nortriptyline, protriptyline, imipramine, amitryptyline, trimipramine, and doxepin and different from the serotonin reuptake inhibitors (SRIs), e.g. fluoxetine, sertraline and paroxetine.

It is believed that venlafaxine's mechanism of action is related to potent inhibition of the uptake of the monoamine neurotransmitters serotonin and norepinephrine. To a lesser degree, venlafaxine also inhibits dopamine reuptake, but it has no inhibitory activity on monoamine oxidase. O-desmethylvenlafaxine, venlafaxine's major metabolite in humans, exhibits a similar pharmacologic profile. However, venlafaxine's ability to inhibit norepinephrine and serotonin (5-HT) uptake has been predicted to have an effect not just on depression but also on reproductive function through its neurotransmitter effects on the hypothalamic-pituitary-ovarian (HPO) axis.

DESCRIPTION OF THE INVENTION

The hypophysiotropic area of the hypothalamus is rich in biogenic amines (e.g., norepinephrine (NE), serotonin (5-HT) and dopamine (DA)) that can affect both the central nervous system (CNS) and endocrine system. The synthesis and release of pituitary hormones are controlled by releasing and inhibitory homones that are found in this anatomical area and controlled by the neurotransmitters 5-HT, norepinephrine, and dopamine whose afferents are located in the hypophysiotropic area and originate in the hypothalamus and in higher centers.

Altered levels of central neurotransmitters can result in a dysfunctional CNS and, in some cases, with consequent profound effects on the hypothalamic pituitary axis (HPO) resulting in impaired reproductive function.

An excess of central biogenic amines can result in altered pulse frequency and irregular amplitude of gonadotropin releasing hormone (GnRH) secretion. These changes lead to disruption of GnRH cyclicity and pituitary down-regulation by desensitization of pituitary receptors resulting in impaired secretion of luteinizing hormone (LH) and follicle stimulating hormone (FSH) and consequent impaired gonadal function. On the other hand, a deficiency of central biogenic amines decreases the synthesis and release of GnRH, but cyclicity may be normal. The effects on the pituitary are a decreased number of receptors leading to impaired secretion of LH and FSH and consequent impaired gonadal function. Thus, either excess or deficiency of neurotransmitters (namely, norepinephrine, serotonin and dopamine) may lead to impaired gonadal function.

The CNS and Endocrine systems are inextricably linked and psychotropic drugs will invariably have some measurable effect on both systems. However, in the case of hypothalamic amenorrhea, one can determine the direct effect on the hypothalamic hormones by measuring gonadotropin-releasing hormone (GnRH), LH, itself, as well as the more objective endpoint of return of menses. These measures distinguish quite clearly an effective physical endpoint distinct from depression endpoints rendering depression scoring systems irrelevant. This proposed treatment is designed to cure an endocrinopathy with or without accompanying comorbidity (depression). The aim or goal of the therapy is the return of normal reproductive function.

Present therapy for hypothalamic amenorrhea uses GnRH delivered I.V. in pulsatile fashion as well as using other invasive supportive therapy, e.g. injections of human chorionic gonadotropin (HCG). The present invention delivers oral doses without the need for supportive ancillary therapy or the use of invasive techniques.

Hypothalamic amenorrhea, also known as secondary amenorrhea is the pathological absence of menstruation due to abnormal centrally mediated neuroendocrine responses affecting the hypothalamic-pituitary-ovarian axis. This cessation of menses may result following a number of occurrences, including severe stress, emotional disturbances or continuous strenuous exercise as in runners or ballet dancers, or sudden loss of body mass (anorexia nervosa), etc. unrelated to depression.

Hypothalamic amenorrhea occurs in about 5% of all menstruating women, with age distribution ranges from approximately 18 years (15%) to 41+ years (21%), reaching a maximum of 52% between ages 22 and 29. It is characterized by low to normal gonadotropins and failure to demonstrate withdrawal bleeding. It is not characterized by depression. Stressful events are known to precipitate anemorrhea and the symptoms can last from a few months to years. Infertility is the usual sequelae following loss of ovulation and menses. This disorder is usually diagnosed by an exclusionary process with particular attention to the existence of pituitary tumors. Patients suffering from hypothalamic amenorrhea have low to normal gonadotropins and some stressful event has often occurred prior to onset of the disorder. The resultant sequelae, i.e., anovulation and amenorrhea, can usually be traced to abnormal Gonadotropin Releasing Hormone (GnRH) rhythms and the restoration of normal rhythm and cyclicity, such as by the practice of the present invention, leads to a resumption of menses, ovulation and hence fertility. The method of the present invention is particularly of interest for the treatment of hypothalamic amenorrhea in non-depressed women who are otherwise physically and mentally normal.

The present invention provides a method for treating hypothalamic amenorrhea in a non-depressed mammal, preferably in a non-depressed human female. This method involves administering to the mammal one or more compounds from a group of substituted phenethylamines following the structural formula:

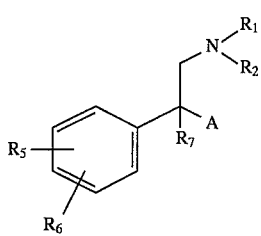

in which A is a moiety of the formula

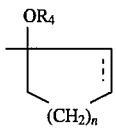

wherein
the dotted line represents optional unsaturation;
$R_1$ is hydrogen or alkyl of 1 to 6 carbon atoms;
$R_2$ is alkyl of 1 to 6 carbon atoms;
$R_4$ is hydrogen, alkyl of 1 to 6 carbon atoms, formyl, or alkanol of 2 to 7 carbon atoms;
$R_5$ and $R_6$ are independently hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkylamino of 1 to 6 carbon atoms, dialkylamino in which each alkyl group is of 1 to 6 carbon atoms, alkanamido of 2 to 7 carbon atoms, halo, trifluoromethyl, or when taken together, methylenedioxy;
$R_7$ is hydrogen or alkyl of 1 to 6 carbon atoms; and n is one of the integers 0, 1, 2, 3, or 4;
or a pharmaceutically acceptable salt thereof.

The preferred compounds are those of the formula:

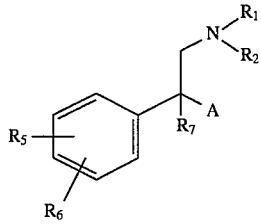

in which
A is as defined supra;
$R_1$ is hydrogen or alkyl of 1 to 3 carbon atoms;
$R_2$ is alkyl of 1 to 3 carbon atoms;
$R_3$ is hydrogen, hydroxy, alkoxy of 1 to 3 carbon atoms, chloro, bromo, trifluoromethyl or alkyl of 1 to 3 carbon atoms;
$R_5$ is hydrogen, hydroxyl, alkoxy of 1 to 3 carbon atoms, chloro, bromo, trifluoromethyl or alkyl of 1 to 3 carbon atoms;
$R_6$ is alkyl of 1 to 3 carbon atoms, alkoxy of 1 to 3 carbon atoms, chloro, bromo, trifluoromethyl or alkanoyloxy of 2 to 3 carbon atoms;
$R_7$ is hydrogen or alkyl of 1 to 3 carbon atoms;
or a pharmaceutically acceptable salt thereof.

The most preferred compounds are those in which both $R_5$ and $R_6$ are in meta positions, or one of $R_5$ and $R_6$ is in the para position, and n is 2.

Of particular interest are the compounds 1-[(2-dimethylamino)-1-(4-methoxyphenyl)ethyl]cyclohexanol and 1-[(2-dimethylamino)-1-(4-hydoxyphenyl)ethyl]cyclohexanol and pharmaceutically acceptable salts thereof.

The compounds in which $R_4$ is formyl or alkanoyl of 2 to 7 carbon atoms have been found to be not as potent as the corresponding free hydroxy bearing derivatives. However, in long term therapy the acyloxy derivatives will act as pro drugs as the acyl group is removed in vivo either via acid hydrolysis in the stomach or enzymatically.

For the purposes of this disclosure and the claims that follow, it is understood that the use of venlafaxine in treating hypothalamic amenorrhea includes the use of venlafaxine's free base, its pharmaceutically acceptable salts, its racemate and its individual enantiomers, and venlafaxine analogs, both as racemates and as their individual enantiomers.

The pharmaceutically acceptable acid addition salts of the basic compounds of this invention are formed conventionally by reaction of the free base with an equivalent amount of any acid which forms a non-toxic salt. Illustrative acids are either inorganic or organic, including hydrochloric, hydrobromic, fumaric, maleic, succinic, sulfuric, phosphoric, tartaric, acetic, citric, oxalic, and similar acids. For parenteral administration, the use of water soluble salts is preferred, although either the free base of the pharmaceutically acceptable salts are applicable for oral or parenteral administration of the hypothalamic amenorrhea treating agents of this invention. The halo substituent representing $R_5$ or $R_6$ is intended to include the chloro, bromo, iodo, or fluoro substituents.

Pharmaceutical compositions containing the compounds of this invention represent an additional aspect of this invention. The active ingredient can be compounded into any of the usual oral dosage forms including tablets, capsules and liquid preparations such as elixirs and suspensions containing various coloring, flavoring, stabilizing and flavor masking substances. For compounding oral dosage forms, the active ingredient can be mixed with various conventional tabletting materials such as starch, calcium carbonate, lactose, sucrose and dicalcium phosphate to aid the tabletting or capsulating process. Magnesium stearate, as an additive, provides a useful lubricant function when desired.

The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example, packeted powders or vials or ampoules. The unit dosage form can be a capsule, cachet or tablet itself, or it can be the appropriate number of any of these in package form. The quantity of the active ingredient in a unit dose of composition may be varied or adjusted from about 1 mg. or less to about 25 mg. or more, according to the particular need and the activity of the active ingredient. The usual oral recommended dose of venlafaxine for humans may be between about 25 and about 200 mg/day or higher, not to exceed about 375 mg/day, and this dose may be administered in divided doses, preferably with food if administered orally. A maximum recommended daily dose for humans would be about 225 mg. The treatment regimen may start with the lowest dosage, such as 25 mg, and the dose may be titrated upward incrementally, such as in 25 mg increments, up to the maximum recommended dosage. The incremental increases in dosage may be conducted at monthly intervals until menses is resumed at normal cyclic intervals. At the discretion of the attending physician, the compounds of this invention may also be administered at other than daily doses.

It will be understood by one skilled in the art that doseage under this invention will be determined by the particular circumstances surrounding each case, as will the route of administration (e.g. via an oral route, transdermal route, via a pharmaceutical implant, etc.). It is understood that, while it is preferable that the compounds and pharmaceutical formulations of this invention comprise an oral dosage form, such as capsules or tablets, this invention is intended to cover any means of administration to a patient of an active amount of the compounds listed above in the treatment of hypothalamic amenorrhea. Such administrations may also be provided in a bolus form, intermittent-release form, sustained oral administration form or time-release form, which may be used to spread the doseage over time, such as for once-a-day applications.

It should also be understood that the present invention is intended to include all methods of, and reasons for, treating hypothalamic amenorrhea in a non-depressed mammal, preferably in a non-depressed human, by administering to the individual an effective amount of venlafaxine or its analogues or pharmaceutically acceptable salts. For the purposes of the present invention, treating hypothalamic amenorrhea is to be understood as covering all prophylactic, therapeutic, progression inhibiting, remedial, maintenance, curative or other administrations, regimens or treatments of or with venlafaxine or its analogues or salts that yield the desired reduction of the effects of hypothalamic amenorrhea in a non-depressed mammal, preferably in a non-depressed human female.

What is claimed:

1. A method of treating hypothalamic amenorrhea in a non-depressed female mammal, the method comprising administering to the non-depressed female mammal an effective amount of a compound of the formula:

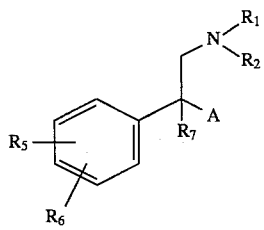

in which A is a moiety of the formula

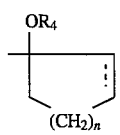

wherein
the dotted line represents optional unsaturation;
$R_1$ is hydrogen or alkyl of 1 to 6 carbon atoms;

$R_2$ is alkyl of 1 to 6 carbon atoms;

$R_4$ is hydrogen, alkyl of 1 to 6 carbon atoms, formyl, or alkanol of 2 to 7 carbon atoms;

$R_5$ and $R_6$ are, independently, hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkylamino of 1 to 6 carbon atoms, dialkylamino in which each alkyl group is of 1 to 6 carbon atoms, alkanamido of 2 to 7 carbon atoms, halo, trifluoromethyl, or taken together, methylene dioxy;

$R_7$ is hydrogen or alkyl of 1 to 6 carbon atoms; and n is 0, 1, 2, 3, or 4;

or a pharmaceutically acceptable salt thereof.

2. The method of claim 1 in which the non-depressed female mammal is a human.

3. The method of claim 1 wherein the compound of the formula:

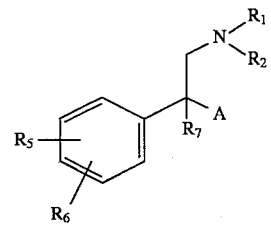

in which A is a moiety of the formula

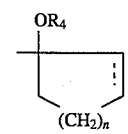

wherein
the dotted line represents optional unsaturation, and
$R_1$ is hydrogen or alkyl of 1 to 3 carbon atoms;
$R_2$ is alkyl of 1 to 3 carbon atoms;
$R_5$ is hydrogen, hydroxyl, alkoxy of 1 to 3 carbon atoms, chloro, bromo, trifuoromethyl or alkyl of 1 to 3 carbon atoms;
$R_6$ is alkyl of 1 to 3 carbon atoms, alkoxy of 1 to 3 carbon atoms, chloro, bromo, trifluoromethyl or alkanoyloxy of 2 to 3 carbon atoms;
$R_7$ is hydrogen or alkyl of 1 to 3 carbon atoms;
or a pharmaceutically acceptable salt thereof.

4. The method of claim 3 wherein $R_5$ and $R_6$ are both in meta positions, or one of $R_5$ and $R_6$ is in the para position, and n is 2.

5. The method of claim 3 wherein the compound is 1-[(2-dimethylamino)-1-(4-methoxyphenyl)ethyl]cyclohexanol or a pharmaceutically acceptable salt thereof.

6. The method of claim 3 wherein the compound is 1-[2-(dimethylamino)-1-(4-hydroxyphenyl)ethyl]cyclohexanol or a pharmaceutically acceptable salt thereof.

7. The method of claim 3 in which the non-depressed female mammal is a human.

8. The method of claim 1 wherein the effective amount comprises a daily dose of between about 1 mg/day and about 375 mg/day.

9. The method of claim 1 wherein the effective amount comprises a daily dose of between about 25 mg/day and about 225 mg/day.

10. The method of claim 1 wherein the effective amount comprises a daily dose of between about 75 mg/day and about 200 mg/day.

11. The method of claim 3 wherein the effective amount comprises a daily dose of between about 1 mg/day and about 375 mg/day.

12. The method of claim 3 wherein the effective amount comprises a daily dose of between about 25 mg/day and about 225 mg/day.

13. The method of claim 3 wherein the effective amount comprises a daily dose of between about 75 mg/day and about 200 mg/day.

* * * * *